US00PP07915P

United States Patent [19]

Warriner

[11] Patent Number: Plant 7,915

[45] Date of Patent: Jul. 21, 1992

[54] ROSE PLANT JACTINE

[75] Inventor: William A. Warriner, Tustin, Calif.

[73] Assignee: Bear Creek Gardens, Inc., Medford, Oreg.

[21] Appl. No.: 625,931

[22] Filed: Dec. 10, 1990

[51] Int. Cl.[5] ..... A01H 5/00

[52] U.S. Cl. ..... Plt./14

[58] Field of Search ..... Plt./11, 14, 15

*Primary Examiner*—Howard J. Locker

*Attorney, Agent, or Firm*—Klarquist, Sparkman, Campbell, Leigh and Whinston

[57] ABSTRACT

A hybrid tea rose plant having unique pale yellow bud that fades to white on the outer petals as the flower opens, dark green leathery glossy foliage, resistance to mildew and rust, thick leathery petals, excellent exhibition bud form and sweet pleasant fragrance.

1 Drawing Sheet

The present invention relates to a new and distinct variety of rose plant of the hybrid tea class which was originated by me by crossing the variety Pristine, U.S. Plant Pat. No. 3,997, with the variety Antigua, U.S. Plant Pat. No. 3,431.

The primary objective of this breeding was to produce a new rose variety having the flower form of Pristine combined with the excellent foliage and higher petal count of Antigua. It was also hoped to create a flower color somewhere between Pristine and Antigua. The objective was substantially achieved along with other desirable improvements as evidenced by the following unique combination of characteristics which are outstanding in the new variety and which distinguish it from its parents, as well as from all other varieties of which I am aware:

1. Unique pale yellow bud that fades to white on the outer petals as the flower opens.
2. Dark green leathery glossy foliage.
3. Resistance to mildew and rust.
4. Thick leathery petals.
5. Excellent exhibition bud form.
6. Sweet pleasant fragrance.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color description using terminology in accordance with The Royal Horticultural Society (London) Colour Chart, except where ordinary dictionary significance of color is indicated.

Parentage:

*Seed parent.*—Pristine, U.S. Plant Pat. No. 3,997.

*Pollen parent.*—Antigua, U.S. Plant Pat. No. 3,431.

Classification:

*Botanical.*—*Rosa hybrida.*

*Commercial.*—Hybrid tea.

FLOWER

Observations made from specimens grown in a garden in Somis, Calif. in Sep., 1990.

Blooming habit: Recurrent.

Bud:

*Size.*—1¾ to 2 inches when the petals start to unfurl.

*Form.*—Long, pointed ovoid.

*Color.*—When sepals first divide, bud color is Yellow Group 13C. When half blown, the upper sides of the petals are Yellow Group 8D on the outer petals, deepening to Yellow Group 8C in the center; and the lower sides of the petals are Yellow Group 8D.

*Sepals.*—Color: Green Group 138D. Surface texture: Covered with fine hairs. There are three normally appendaged sepals. There are two unappendaged sepals with hairy edges.

*Receptacle.*—Color: Green Group 137C. Shape: Funnel. Surface: Smooth.

*Peduncle.*—Length: Medium (3 to 3½"). Surface: Glandular. Color: Medium green. Strength: Stiff, erect.

Bloom:

*Size.*—Large. Average open size is 5 to 5½ inches.

*Borne.*—Singly.

*Stems.*—Medium (14 to 18"), strong.

*Form.*—When first open: High center. Permanence: Retains its form to the end, outer petals curl back.

*Petalage.*—Number of petals under normal conditions: 30.

*Color.*—The upper side of the petals is Yellow Group 8D, deepening to Yellow Group 8C in the center of the flower. The reverse side of the petals is Yellow Group 8D. The color of the base of petals intensifies to Yellow Group 8A at the petal base. The major color on the upper side is Yellow Group 8D.

*Variegations.*—None.

*Discoloration.*—No general tonality change at the end of the first day. At the end of the third day, as the flower opens and more petal surface is exposed to sunlight, there is a gentle fading to Yellow Group 8D over an increasingly greater surface area of the petals.

*Fragrance.*—Moderate.

Petals:

*Texture.*—Thick, leathery.

*Shape.*—Round to deltoid.

*Form.*—Tips slightly recurved.

*Arrangement.*—Imbricated, with few petaloids in the center.

*Persistence.*—Drop off cleanly.

*Lastingness.*—On the plant: Long (about 5 days). As a cut flower: Long (about 7 days).

Reproductive parts:

*Anthers.*—Size: Large. Quantity: Many. Color: Yellow. Arrangement: Regular around styles.

*Filaments.*—Color: Yellow.

*Pollen.*—Color: Gold Yellow.

*Styles.*—Color: Red.

*Stigmas.*—Color: Greenish white.

Form: Bush.

Growth: Vigorous, upright, branching.

Foliage:

*Number of leaflets on normal mid-stem leaves.*—5 or 7.

*Size.*—Large (6"×4½").

*Quantity.*—Abundant.

*Color.*—New foliage: Reddish. Old foliage: Dark glossy green.

Leaflets:

*Shape.*—Pointed oval.

*Texture.*—Upper side: Leathery, glossy.

*Edge.*—Serrated.

*Serration.*—Single, small.

*Petiole rachis.*—Color: Reddish.

*Petiole underside.*—Rough with prickles.

*Stipules.*—Long (¾ to 1"), bearded.

Disease resistance: Resistant to mildew and rust under normal growing conditions at Somis, Calif.

Wood:

*New wood.*—Color: Reddish. Bark: Smooth.

*Old wood.*—Color: Green. Bark: Smooth.

Prickles:

*Quantity.*—On main canes from base: Many. On laterals from main canes: Many.

*Form.*—Medium (¼"), hooked downward.

*Color when young.*—Red.

Small prickles:

*Quantity.*—On main stalks: None. On laterals: None.

I claim:

1. A new and distinct variety of rose plant of the hybrid tea class, substantially as herein shown and described, characterized particularly as to novelty by the unique combination of its novel light yellow fading to white on the outer petals flower color, its dark green leathery and disease resistant foliage, its thick leathery petals, its excellent exhibition flower form and its sweet pleasant fragrance.

* * * * *

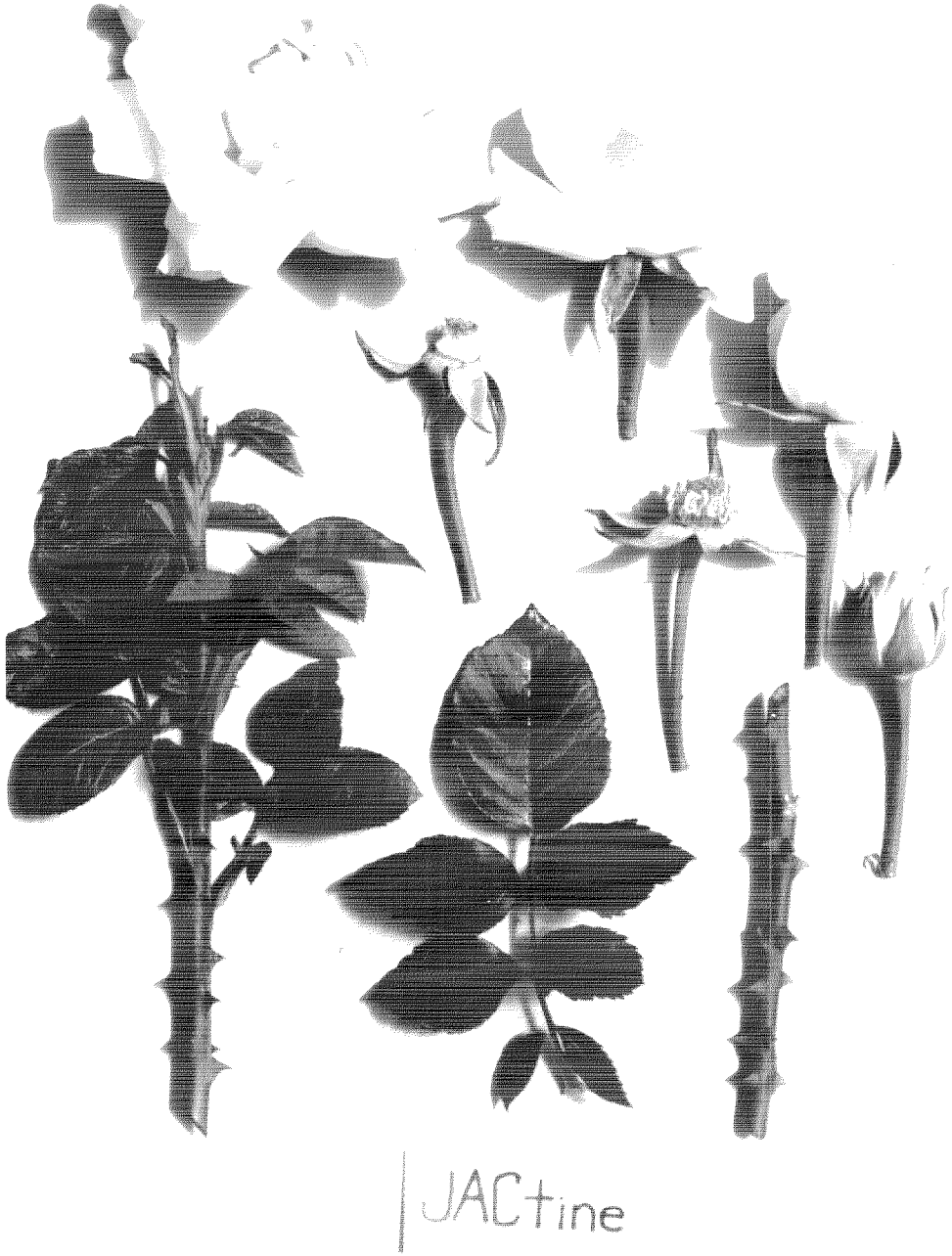
JACtine